United States Patent [19]

Salbaum et al.

[11] Patent Number: 5,151,508

[45] Date of Patent: Sep. 29, 1992

[54] PROMOTER REGION FOR DNA SEQUENCES WHICH ENCODE THE PRECURSOR OF THE HUMAN A4 AMYLOID PROTEIN

[75] Inventors: Johannes M. H. Salbaum, Waldkirchen, Fed. Rep. of Germany; Colin L. Masters, Darlington, Australia; Konrad T. Beyreuter, Heidelberg, Fed. Rep. of Germany

[73] Assignee: Molecular Therapetuics, Inc., West Haven, Conn.

[21] Appl. No.: 393,360

[22] Filed: Aug. 14, 1989

Related U.S. Application Data

[63] Continuation-in-part of Ser. No. 385,758, Jul. 26, 1989, abandoned.

[30] Foreign Application Priority Data

Aug. 30, 1988 [GB] United Kingdom ................ 8820450

[51] Int. Cl.$^5$ ...................... C07H 15/12; C12N 15/00
[52] U.S. Cl. .................................. 536/27; 435/320.1; 935/6
[58] Field of Search ............ 435/69.1; 800/2, DIG. 2; 935/6, 23

[56] References Cited

PUBLICATIONS

Kang et al. (1987) The Precursor to Alzheimer's Disease Amyloid A4 protein . . . *Nature* 325, 733–736.
Scangos et al. (1987) *Gene Transfer into Mice,* Advances in Gentics vol. 24, 285–322.
Riccio et al. (1985) The Human Urokinase–plasminogen activator gene and its promoter, *Nucleic Acids* Res. 13, 2759–2771.

*Primary Examiner*—Elizabeth C. Weimar
*Assistant Examiner*—Deborah Crouch
*Attorney, Agent, or Firm*—Sprung Horn Kramer & Woods

[57] ABSTRACT

The present invention is related to the promoter of the gene for the human precursor of the Alzheimer's Disease A4 amyloid protein (PAD gene).

Another object of the present invention is the use of this promoter in a method of establishing a screening model for the Alzheimer's Disease. Thus the present invention is also related to a vector useful in the transfection of cells and the cells and animals transfected therewith.

8 Claims, 4 Drawing Sheets

```
               10         20         30         40         50
       BamHI    .          .          .          .          .
       GGATCCTAA CCCAATATCT GCTGTCCTTA TAACAAGAGG AGATTAGGGC
       ACAGTAAGAC ACAGAGGGAA GACCATGTGA GAATACAGGG AGAAGGTGGC
       CATCTGCAAG CCAAGGAGAG AGGCCTCAGA AGTAACCAAC TCAGCCAACA
       CCTCGATTTC AGACTTCCAG CCTCCTGAAA TGTGAGGAAA TACATTTCTG
-3500  GTGTTTGATC CATCCAGTCT ATGGTAAGTT ATGGCACCCT GCAGGGTTCA
       TCTGGCTCAG ACTTAACGAT TGCTTTTGGT GATATTTATA GGGCACAGAT
       AACAGCCTAA ACACAAGACG ACAGAAACGC GGCCCAGCAG ACTATGCATA
       AAATAGAAAT GGGGTATCTG GACCAATTGG AGTCTGCAGT GGGATCCGGT
       TACTAAAACA GTCAAATGCA ACATGAGGCT CCAGGCAGAG TAGTGGGCAA
       CATCTCCCAT GTTGCAGCAG TCAGAGCACA CTTCGAGTAC TGTAAAAAGA
       CACAGACAAG GCAGAACACT TTAGAGAATG GCCAAGGTGT GGAAGGAACG
       AGAAACCATG CCATTATGCA ACTGTTGAAG GAAGTGCCTG TTTTACCTTG
       TGAAGAGAAG ACTCTAGAGG AAGAAGTAGC ATGAAAACAG CTGGCAAATT
       TGTAAAGATC TGAAGTGTGC AAAAGAATTA TTCTGCTTGG TCACTGGGCA
-3000  ATACAAGGAT ATCTGAGTGG GAGTTTAAAG GCGGGGGATG TGAGCTTTAA
       ATGGGATAAG AACATTCTAG TAACCAGAAA TGCCCAAAGA TAGAATGCAC
       AGTCTGGAGA GCCAGTGAAT ATCTCACAAA TGGAGACACT TGAAACTAGG
       ATGGGGATGC TGTTGTAGGA ATTCCAGCAG ACAAGTGGTT GTTGGTTCCT
       TCCCCAACTT TGTAGGGTTA TAACTAGGGA TGTTCCTGCG TTTTCTGCTT
       GGAGGATCTG CAAGACACCT CAGGGCAGGA AATGGCATTA AATGCAGAAC
       AGAGCTAGTG GCTGAAAAGC AAAAAGCCAT CAGGATCTCT GGAGTAGTGA
       AGGAACCAGA GAACATGCAG GCAATGTCCA TCATTCTGAC GCAATCAGCA
       GCGATAATCA TCTTCCCCCA GGAACATCTT GACCAGGGAA TGTGTCAGTG
       TTGGTGAATT TCAACAGTGG AAAGAGAAAC TGCTAAATCT AAGAACTTTA
-2500  ATTTTTATAG GTTATGATCT CATCTCTACA ATTTGAATT TCATGCTCAA
       TAAAAGTTCC TTACTCTCTT TTTTTTTTT TGAGACGGAG TCTCGCTCTG
       TCGCCCAGGC TGGAGTGCAG TGGCGCGATC TCGGCTCACT TCAAGCTCAG
       CTCCCGGGTT CACGCCATTC TCCTGCCTCA GCCTCCCAGT AGCTGGGACT
```

FIG.1A

```
        ACAGCGCCCG CCACGACGCC CGGCTAATTT TTTGTATTTT TAGTAGAGAC
        GGGGTTTCAC CGTGTTAGCC AGGATGGTGT TGATCTCCTG ACCTCGTGAT
        CCGCCCGCCT CAGCCTCCCA AGAAAAGTC CCTCACTCTT AAAGTTGCCT
        CCTCCTTCCC AGGGCTGGCT TCATGGGCAT CCAACCCTCC AGAGTCTCAC
        AGGCCCTGCG GTGGGAGGAG CCCCATGCTT GGTTTAACGC TCTGCCATTG
        CCATCTTAAA ATTCTTAATT TAATTTTTTT TCTTTTTTTT TGAGGTGGAG
-2000   TCTCGCTCTG TCGCCCAGGC TGGAGTGCAA TGGCACAATC TTGGCTCACT
        GCAACCTCCG CCTCCCAGGT TCAAGCGATT CTCCTGCCTC AGCCTCTGGA
        GTAGCTGGGA TTACAGGCAG GAGTAACCAC GCTCGGCTAA TTTTTGCATT
        TTTAGTAGAC ATGGGGGTTT CACCATGTTG GCCAGGCTGG TCTAGAACTC
        CTGACCTCAG GTGATCTCCC ACCCTGGGCC TCCTAAAGTG CTGGGATTAC
        AGGCATGAGC CACCAGGCCC GGCCTTAAAA TTCTTAATAA TGTAACAAAG
        GGTCTCACGT TTGCATTTTG CAGTGGACTC TGCAAGATTG TAGCTTGGAC
        CACGTTCTCT TGCATTCAGA TACCTTCTTT TTGCCTTATT TGCTCATGCA
        GACCCGGAAC AAATACGGAA TTGCGGTGGT AAATGTGGTG CAGAAAGTGA
        ACAACTGGGT TTGTCCTGTC ACTTAGGCT TTTCCCTGTG TCCCAGCTTC
-1500   ATGTCACTTA CTTGCTATTA GATTTGGGAG TTCATTAGCT TCATTTTCCT
             10         20        30        40        50

GATGTATAAA TAGGAATAAT AGTAACAGCC TCTTTGGCTT TTGTAGGAAG
        TAAATGACAT GAAGCGTATA AACAAATACT GCATGACAAT AAATATTTGT
        CCTTATTTGT TGAGGACATC CAAAGGACAT TCAGGGGCAA AAGTAATCCA
        AGAGTCAAGA CTGAATGCCT AGTGCGGAAA AAGACACACA AGACAACATT
        TAGGGGAGCT GGTACAGAAA TGACTTCCCA GAAGAAGTCT GTACCCCGCT
        GCCTGAGCCA TCCTTCCCGG GCCTCGGCAC CCTTGTCAGC GCAATGAGCA
        AGGGAGAGAA GGCAGCAGTG CAGCCTCAGA AGGGCCAGCG CACTCCCTGG
        CTTCAGTCCT TCGCTCCAAG CCCTGTGTGG AGTGGGCTGT GGCTTGGTAA
        CTAAACGCTA CTTCAGGTCA AGAGCAGGGG ATATATCTGG GCAGTTCTAG
-1000   AGCATTCTAA ACTATCTGGA CACTAACTGG ACAGTGGACG GTTTGTGTTT
        AATCCAGGAG AAAGTGGCAT GGCAGAAGGT TCATTTCTAT AATTCAGGAC
```

FIG.1B

```
-900  AGACACAATG AAGAACAAGG GCAGCGTTTG AGGTCAGAAG TCCTCATTTA
      CGGGGTCGAA TACGAATGAT CTCTCCTAAT TTTTCCTTCT TCCCCAACTC
-800  AGATGGATGT TACATCCCTG CTTAACAACA AAAAAGACC CCCCGCCCCG
      CAAAATCCAC ACTGACCACC CCCTTTAACA AACAAAACC AAAAACAAAC
-700  AAAAATATAA GAAAGAAACA AAACCCAAGC CCAGAACCCT GCTTTCAAGA
      AGAAGTAAAT GGGTTGGCCG CTTCTTTGCC AGGGCCTGCG CCTTGCTCCT
-600  TTGGTTCGTT CTAAAGATAG AAATTCCAGG TTGCTCGTGC CTGCTTTTGA
      CGTTGGGGGT TAAAAAATGA GGTTTTGCTG TCTCAACAAG CAAAGAAAAT
              HindIII
-500  CCTATTTCCT TTAAGCTTCA CTCGTTCTCA TTCTCTTCCA GAAACGCCTG CCCCACCTCT CCAAACCGAG AGAAAAAACG AAATGCGGAT AAAACGCAC
                                       MspI
-400  CCTAGCAGCA GTCCTTTATA GCACACCCCC GGGAGGCCTG CGGGGTCGGA TGATTCAAGC TCACGGGGAC GAGCAGGAGC GCTCTCGACT TTTCTAGAGC
      ─────────                          *     * 
              *
-300  CTCAGCGTCC TAGGACTCAC CTTTCCCTGA TCCTGCACCG TCCCTCTCCT GGCCCCAGAC TCTCCCTCCC ACTGTTCACG AAGCCCAGGT GGCCGTCGGC
     MspI
-200  CGGGGAGCGG AGGGGGCGCG TGGGGTGCAG GCGGCGCCAA GGCGCTGCAC
         ──────  ──────────
                                 MspI
      CTGTGGGCGC GGGGCGAGGG CCCCTCCCGG CGCGAGCGGG CGCAGTTCCC
          ─────                   ──   ───  ───
     MspI                                       MspI
-100  CGGCGGCGCC GCTAGGGGTC TCTCTCGGGT GCCGAGCGGG GTGGGCCGGA -50   TCAGCTGACT CGCCTGGCTC TGAGCCCCGC CGCCGCGCTC GGGCTCCGTC
           ────  ─                                      ''
+1    AGTTTCCTCG GCAGCGGTAG GCGAGAGCAC GCGGAGGAGC GTGCGCGGGG
        ''
        MspI
+51   GCCCCGGGAG ACGGCGGCGG TGGCGGCGCG GGCAGAGCAA GGACGCGGCG
      BamHI
+101  GATCC
```

FIG. 1C

PROMOTER REGION FOR DNA SEQUENCES WHICH ENCODE THE PRECURSOR OF THE HUMAN A4 AMYLOID PROTEIN

CROSS REFERENCE TO RELATED APPLICATION:

This application is a continuation-in-part application of application Ser. No. 07/385,758, filed Jul. 26, 1989, now abandoned.

The present invention is related to the promoter of the gene for the human precursor of the Alzheimer's Disease A4 amyloid protein (PAD gene).

Another object of the present invention is the use of this promoter in a method of establishing a screening model for the Alzheimer's Disease. Thus the present invention is also related to a vector useful in the transfection of cells and the cells and animals transfected therewith.

The pathological hallmark of Alzheimer's disease (AD) is the deposition of fibrillar aggregates of the 42/43-residue amyloid A4 protein (also termed β-protein) (Glenner and Wong, 1984, Biochem. Biophys. Res. Commun., 122, 885-890), Masters et al., (1985) Poc. Natl. Acad. Sci. USA, 82, 4245-4249, EMBO J., 11, 2757-2763. Protein sequencing of amyloid isolated from brain of patients with AD and aged individuals with Down's syndrome (DS) revealed the presence of the A4 protein in both conditions (Beyreuther et al., (1986) Discussions in Neuroscience, 3, 68-79).

Recently, molecular cloning based on the sequence of the A4 protein indicated that it is encoded as part of a larger precursor (PreA4) that maps to chromosome 21 (Kang et al., (1987) Nature, 325, 733-736; Goldgaber et al., (1987) Science, 235, 877-880; Tanzi et al., (1987) Science, 235, 880-884). Two mRNA-bands (Kang et al., (1987) Nature, 325, 733-736) have now been accounted for by the demonstration of three alternative splicing products of the amyloid gene (Ponte et al. (1988) Nature, 331, 525-527; Tanzi et al., (1988) Nature, 331, 528-530; Kitaguchi et al., (1988) Nature, 331, 530-532). The smallest of these products, the 695-residue precursor protein (PreA4$_{695}$), has been synthesized in vitro and shown to be a N-glycan membrane protein that spans the lipid bilayer once (Dyrks et al., (1988) EMBO J., 7, 949-957). At least two other forms of PreA4 exist (PreA4$_{751}$ and PreA$_{751}$ and PreA$_{770}$), both containing a 56 residue insert which has a protense-inhibitory function. The amyloidogenic A4 protein is derived in part from the transmembrane domain and from part of the adjacent extracellular N-glycan domain. A precursor-product relationship has been demonstrated. This suggests that membrane damage and proteolytic cleavage could be important events which precede the release of the A4 protein.

The A4 gene is expressed in brain and peripheral tissues, such as muscle and epithelial cells (Goeder, (1987) EMBO J., 6, 3627-3632; Bahmanyar et al., (1987) Science, 237, 77-88; Zimmerman et al., (1988) EMBO J., 7, 367-372; Shivers et al., (1988) EMBO J., 7, in press), yet for reasons still unknown the amyloid deposits in AD are confined to the brain.

Recently, in situ hybridisation analyses were published that indicate an alteration of the amount of PreA4 mRNA in brains of AD patients when compared to normal individuals (Higgins et al., (1988) Proc. Natl. Acad. Sci. USA, 85, 1297-1301) Cohen et al., (1987) Science, 237, 77-88; Lewis et al., (1988) Proc. Natl. Acad. Sci. USA, 85, 1691-169). These results implicate a role for gene regulation in AD.

To express questions about the breakout of that disease, its course and for establishing a drug-screening model it was first deemed to be necessary to isolate the promoter of the amyloid A4 precursor gene.

DESCRIPTION OF THE FIGURES

FIG. 1A-C is the nucleotide sequence of the 3.8 kb Bam H1 fragment of clone PN-1 which contains the promoter region for the precursor to the human A4 amyloid protein.

Materials and Methods

Cloning and DNA Sequencing

Figure 2:
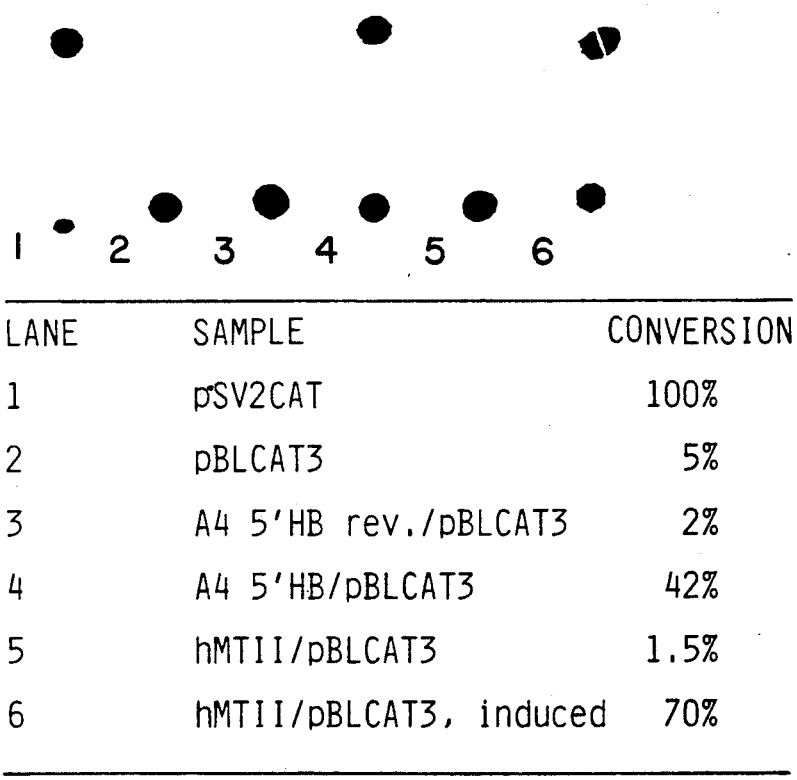
FIG. 2 demonstrates promoter function measured by chloramphenicol acetyltransferase activity. Plasmid constructs where promoters are operatively linked to the CAT gene were transfected into HeLa cells. Lane 1: pSV2CAT; Lane 2: CAT gene without a promoter; Lane 3: promoter region for the precursor to the human A4 amyloid protein in reverse orientation; Lane 4: promoter region for the precursor to the human A4 amyloid protein in correct orientation; and Lane 5: human metallothionein promoter.

Clone H1, 30 was isolated from a chromosome 21 library using the BamHI AccI fragment (−47 to +27, Kang et al., (1987) Nature, 325, 733-736) of the PreA4$_{695}$ cDNA as probe. Hybridisations were performed in 5×SSPE, 50% formamide, 1×Denhardt's solution, 1 mM EDTA at41° C. with 10$^6$ cpm/ml of randomly primed probe (Feinberg and Vogelstein, (1984) Anal. Biochem., 137, 266), A 593 bp HindIII BamHI fragment of clone H1.30 was subcloned into M13 vectors and sequenced on both strands. This fragment also was used to screen a human genomic library and to isolate clone PN.1. A 3.8 kb BamHI fragment was subcloned into a Bluescript vector (pKS+, Genofit, Heidelberg). A set of ordered deletions along the DNA was constructed with the help of Exonuclones III and Mung Bean Nuclease (Genofit, Heidelberg), DNA from 12 deletion plasmids was purified on CaCl gradients and used for DNA sequencing. The chain termination method (Sanger et al. (1977) Proc. Natl. Acad. Sci. USA, 74, 5463-5467) was performed using T7 DNA Polymerase (Sequenase, USB) on single stranded as well as on denatured plasmid DNA templates (Chen and Seeburg, (1985) DNA, 4, 165-170).

Nuclease S1 Protection and Primer Extension Analysis

The Nuclease S1 protection assay was performed as described (Ruppert et al. 1986). A uniformly labelled single stranded DNA probe was synthesised by annealing an oligonucleotide primer 5'-GCCGCGTCCTTGCTCTGC-3' to mha6 template DNA (a M13mp19 clone of the 593 bp HindIII BamHI PAD gene 5' end fragment) and extension with Klenow polymerase (Boehringer Mannheim) to the HindIII site. The probe was hybridised to 10 μg of total human fetal brain RNA, digested with S1 nuclease (Boehringer Mannheim) and the resulting products analysed on a 6% sequencing gel.

For primer extension analysis, the same annealing mix as for the S1 probe was prepared. Extension of the oligonucleotide with Klenow polymerase was performed with dGTP,dTTP and α[P$^{32}$]dCTP in the absence of dATP. The resulting 29 bp labelled primer was purified on a 6% denaturing (8M urea) polyacrylamide gel. $10^5$ cpm of primer were annealed to 20 μg of total fetal brain RNA for 30 min at 42° C. in 40 mM TrisCl pH 8.3, 80 mM NaCl, 6 mM $MgCl_2$, 2.5 mM DTT. After addition of all four dNTPs at 0.5 mM and 20 u AMV reverse transcriptase (Genofit, Heidelberg). The reaction was incubated for 30 minutes at 42° C. After ethanol precipitation, products were separated on a 6% sequencing gel and subjected to autoradiography.

In Vivo Promoter Assay

In order to assay in vivo promoter activity, CAT assays in HeLa cells transfected with the appropriate constructs were performed as described (Schöler and Gruss, (1985) Cell, 36, 403-411). The 593 bp HindIII BamHI fragment was cloned into pBLCAT3 (Luckow and Schütz, (1987) Ac. Res., 15, 5490). To generate a construct with the PAD gene promoter in reverse orientation to the CAT gene, the 593 bp HindIII BamHI fragment was treated with Klenow polymerase and cloned via blunt ends into the HincII site of pUC19. The insert of a properly oriented clone was cut out with HindIII and BamHI and cloned into pBLCAT3, pSV2CAT and the hMTII promoter (Karin et al., (1984) Nature, 308, 513-519) cloned into pBLCAT3 were used as controls.

Cloning of the PAD Gene Promoter

Ganomic clones were isolated from the 5' end of the PAD gene. A BamHI AccI fragment from position −47 to +227 of A4 amyloid precursor cDNA (Kang et al., 1987), which encodes the shortest precursor cDNA (Kang et al., 1987), which encodes the shortest 695 residue product (PreA4$_{695}$) was used to screen a library of flow-sorted human chromosome 21. Clone H1.30 was found to contain a 2.8 kb HindIII fragment which was subcloned into pUC19. The fragment contained a single BamHI site. The 593 bp HindIII BamHI fragment of clone H1.30 was cloned into M13 vectors and the DNA sequence of both strands was determined. This DNA fragment was found to contain 99 bp upstream of the BamHI site which were identical to the reported 5' untranslated cDNA sequence of PreA4$_{695}$, except for one additional G in the genomic DNA at cDNA position −96 to −99. The genomic DNA showed a stretch of five consecutive Ga versus four in the cDNA, The 488 bp upstream of the cDNA sequence were expected to be the promoter region of the PAD gene. In order to obtain a clone which contains more upstream DNA, the 593 bp HindIII BamHI fragment was used as a probe to screen a human genomic library, Clone PN,1 was isolated and found to have 3.8 kb BamHI fragment which hybridised to the probe. This fragment was subcloned and its DNA sequence was determined (FIG. 1). The DNA contains two copies of an Alu-type repetitive sequence in the same orientation at positions −2436 to −2179 and −2020 to −1764.

PAD Promoter Elements

The DNA sequence upstream of the multiple RNA 5' termini (FIG. 1) does not contain a typical TATA box and has a high GC content, Between positions −1 and −400 the DNA is comprised of 72% GC. The ratio of the dinucleotide CpG, the target site for DNA methylation, vergus GpC is about 1:1 around the RNA start site. At position −45 as well as −350, relative to the strongest 5' end signal, a heptamer sequences were found which are in good agreement to the binding consensus sequence of the transcription factor AP-1 (TGACTCA, Lee et al., (1987) Nature, 325, 368-372). The sequence starting at position −317 corresponds very well to the heat shock control element (HSE), whose consensus sequence is CT-GAA--TTC-AG (Wu et al., (1987) Science, 238, 1247-1253). Furthermore, six copies of a GC-rich element following a consensus of

can be located between positions −198 and −105. The features of multiple RNA start sites, the absence of a typical TATA box, the high GC content of the DNA upstream of the RNA starts, and the presence of a GC-rich box places the promoter of the PAD gene in the class of promoters of "housekeeping" genes, like the adenosine deaminase gene (Valerio et al., (1985) EMBO J., 4, 437-443) or the gene for dihydrofolate reductase (Crouse et al., (1982) J. Biol. Chem., 257, 1357-1370). The promoter of the hamater PrP gene, the product of which gives rise to brain amyloid deposits in scrapie infected animals, is organised in a similar fashion (Basler et al., (1986) Cell, 46, 417-428).

Promoter Activity in Vivo

The 593 bp HindIII BamHI fragment was tested for its ability to show promoter activity in vivo. It was cloned into pBLCAT3 (Luckow and Schüta, (1987) Ac. Res., 15, 5490) in correct as well as in reverse orientation to the chloramphenicol acetyltransferase (CAT) gene. These constructs were transfected into HeLa cells and CAT activity was measured (FIG. 2). The SV40 promoter of pSV2CAT served as high control (lane 1), resulting in a complete conversion of chloramphenicol into its acetylated derivatives. Transfection with the PAD promoter in reverse orientation yielded 2% conversion (lane 3), comparable to the CAT vector without an inserted promoter (5%, lane 2) or the non-induced human metallolithionine II (hmt II) promoter (1.5%, lane 5). When induced with 2 mM $Zn^{2+}$, the hmt II promoter produced 70% conversion in our assay conditions. The PAD promoter fragment in correct orientation gave 42% conversion (FIG. 2, lane 4). This result clearly shows that the 593 bp genomic fragment can function as a promoter in an in vivo assay. Together with the results of the 5' end mapping of the PreA4$_{695}$ mRNA we conclude that indeed the promoter of the PAD gene has been isolated from the genomic clones.

In the same manner as the CAT gene the human precursor of Alsheimer's Disease A4 amyloid protein of German Patent Application P 3 702 789.1 can be used as reporter gene.

The method of preparing transgenic animals is described in Hogan, B., et al., in Manipulating the Mouse Embryo, A Laboratory Mannual, Cold Spring Harbor Laboratory, 1986.

We claim:

1. The promoter region for DNA sequences which encode the precursor of the human A4 amyloid protein which regulates expression of said DNA sequences.

2. The promoter region of claim 1 having the sequence as depicted in FIG. 1.

3. A vector for transfecting cells, said vector comprising the promotor region according to claim 1.

4. A vector according to claim 3 additionally comprising DNA sequences encoding a reporter protein.

5. A vector according to claim 4 wherein the reporter DNA sequences encode for the precursor of the human A4 amyloid protein or the chloramphenicol acetyltransferase.

6. A cell line transfected with a vector according to claim 3.

7. A cell line transfected with a vector according to claim 4.

8. A cell line transfected with a vector according to claim 5.

* * * * *

UNITED STATES PATENT AND TRADEMARK OFFICE
CERTIFICATE OF CORRECTION

PATENT NO.  : 5,151,508
DATED       : September 29, 1992
INVENTOR(S) : Salbaum, et al.

It is certified that error appears in the above-identified patent and that said Letters Patent is hereby corrected as shown below:

Title Page   [73] Assignee:  After " Molecular " delete
" Therapetuics " and substitute -- Therapeutics --

Signed and Sealed this

Fourth Day of July, 1995

Attest:

BRUCE LEHMAN

*Attesting Officer*   *Commissioner of Patents and Trademarks*